United States Patent
Narayan et al.

(10) Patent No.: US 9,273,180 B2
(45) Date of Patent: Mar. 1, 2016

(54) POLYOLS FROM BIOMASS AND POLYMERIC PRODUCTS PRODUCED THEREFROM

(71) Applicants: Ramani Narayan, Okemos, MI (US); Daniel Graiver, Midlan, MI (US); Elodie Hablot, Lansing, MI (US); Vahid Sendijarevic, Troy, MI (US); Siva Rama Krishna Chalasani, East Lansing, MI (US)

(72) Inventors: Ramani Narayan, Okemos, MI (US); Daniel Graiver, Midlan, MI (US); Elodie Hablot, Lansing, MI (US); Vahid Sendijarevic, Troy, MI (US); Siva Rama Krishna Chalasani, East Lansing, MI (US)

(73) Assignee: Board of Trustees of Michigan State University and Vahid Sendijarevice, joint ownership, Vahid Sendijarevic, MI (US)

( * ) Notice: Subject to any disclaimer, the term of this patent is extended or adjusted under 35 U.S.C. 154(b) by 56 days.

(21) Appl. No.: 14/034,611

(22) Filed: Sep. 24, 2013

(65) Prior Publication Data

US 2014/0171535 A1 Jun. 19, 2014

Related U.S. Application Data

(60) Provisional application No. 61/705,114, filed on Sep. 24, 2012.

(51) Int. Cl.
| | |
|---|---|
| *C08G 63/685* | (2006.01) |
| *C08G 18/38* | (2006.01) |
| *C08G 4/00* | (2006.01) |
| *C08G 18/48* | (2006.01) |
| *C08G 18/66* | (2006.01) |
| *C08G 18/76* | (2006.01) |
| *C08G 71/04* | (2006.01) |
| *C07C 277/08* | (2006.01) |
| *C08G 18/60* | (2006.01) |
| *C07C 269/00* | (2006.01) |
| *C07C 269/04* | (2006.01) |
| *C08G 18/64* | (2006.01) |
| *C08G 101/00* | (2006.01) |

(52) U.S. Cl.
CPC .......... *C08G 63/6854* (2013.01); *C07C 269/00* (2013.01); *C07C 269/04* (2013.01); *C07C 277/08* (2013.01); *C08G 4/00* (2013.01); *C08G 18/3831* (2013.01); *C08G 18/4833* (2013.01); *C08G 18/60* (2013.01); *C08G 18/6446* (2013.01); *C08G 18/6685* (2013.01); *C08G 18/7664* (2013.01); *C08G 71/04* (2013.01); *C08G 2101/0025* (2013.01); *C08G 2101/0083* (2013.01)

(58) Field of Classification Search
CPC .............................. C08G 18/60; C08G 18/6446
See application file for complete search history.

(56) References Cited

U.S. PATENT DOCUMENTS

| | | | | |
|---|---|---|---|---|
| 5,554,721 A | * | 9/1996 | Adler et al. | 528/328 |
| 2010/0305227 A1 | * | 12/2010 | Parker et al. | 521/114 |
| 2014/0235737 A1 | * | 8/2014 | Parker et al. | 521/102 |

* cited by examiner

*Primary Examiner* — Melissa Rioja

(57) ABSTRACT

Polyol compositions containing methane linkages derived from amino acids. The polyols are obtained from the reaction of the carbonate with the cadres in the amino acids. Individual amino acids or mixtures of amino acids that are prepared from the hydrolysis of the proteins can be used.

31 Claims, 2 Drawing Sheets

POLYOLS FROM BIOMASS AND POLYMERIC PRODUCTS PRODUCED THEREFROM

This application claims priority from U.S. Provisional patent application Ser. No. 61/705,114, filed Sep. 24, 2012.

This invention was made with Government support under IIP1214595 awarded by the National Science Foundation. The Government has certain rights in the invention.

BACKGROUND OF THE INVENTION

Over the past decade, there has been an increased interest within the polyurethane industry to use natural oil based polyols, either as stand-alone products or in conjunction with petroleum based polyols. The two main reasons for this growing interest are: heightened awareness of "green" issues that can minimize greenhouse gas emissions as well as reducing the dependency on non-renewable sources.

The use of biomass as raw materials for production of fuels and chemicals to displace fossil resources has been the focus of many research activities. These activities are motivated by the possibility of positive contributions to a sustainable resource supply, enhanced national security, and macroeconomic benefits for local communities and society at large.

Many of these activities were directed toward fuel and energy production (e.g. fermentation of biomass to ethanol and trans esterification of triglyceride oils to biodiesel).

Only limited effort has been directed toward value added industrial products using the protein biomass that is left behind after extracting the oil. The amino acids in the protein are rich in amine, functional groups that can easily be converted to urethanes.

Many such products can be derived from such polyurethanes and include foams, coatings, adhesives, sealants and elastomers, among many others. Currently, only a few of these synthetic polyurethanes contain bio-based components and these are generally prepared by condensation of petroleum-based isocyanates with vegetable oil based polyols.

Furthermore, it is well known that soybean contains much more protein than oil (see FIG. 1). Although the exact composition of the bean depends on many variables including trait, climax, soil, geographical location, maturity, the extraction process, etc.

Typically, the protein content is almost twice the content of the oil (about 38% compared with only 18% oil). Furthermore, the cost of the protein meal is about half the cost of the oil. Thus, the use of the meal as a raw material is attractive considering the economics and its availability. In the United States, soybeans are readily available and are grown in large quantities. After extracting the oil, most of the soy meal is processed toward animal feed, primarily for poultry, swine, cattle, and aquaculture.

A very small portion is refined to soy flour, soy concentrates, and soy isolates for human consumption and only 0.5% is used for industrial applications. The small amounts of meal used for industrial applications include its use as adhesives for plywood and particle board with other minor applications such as additives in textured paints, insecticides, dry-wall tape compounds, linoleum backing, paper coatings, fire-fighting foams, fire-resistant coatings, asphalt emulsions, cosmetics, and printing inks.

Currently, essentially all polyurethanes used in the industry are made by the phosgenation of amines and then reacting the so-produced isocyanates with polyols. The use of phosgene is economical but it is hazardous and can only be done using special equipment due to the extreme toxicity of phosgene and the high volume of HCl by-products. A number of phosgene-free methods for preparing isocyanates have been reported in the literature.

Patent application EP-A 583.637 discloses the decomposition of tri-substituted ureas at elevated temperature (90-400° C.) and in the presence of a solvent, into a volatile mono-isocyanate and a secondary amine of which the boiling point is higher than that of the isocyanate and higher than the reaction temperature.

U.S. Pat. No. 3,936,484 describes the decomposition of tri-substituted ureas at elevated temperatures (above 230° C.) and in the presence of an inert carrier to form isocyanates and amines. The reported isocyanate yield by this method was relatively low from 60 to 88%.

French patent application A 1473821 describes the pyrolysis of substituted ureas in the Liquid phase (temperature less than 200° C.) in the presence of high boiling solvents, into isocyanates and amines. The reaction times, however, by this method are long (6-35 hours) and the isocyanate yield is only a moderate (60-75%).

Several other methods are known (European patent applications EP-A 391716, EPA 402020 and EPA 408277) whereby isocyanates are prepared by thermally decomposing dialkylureas in an inert solvent in the presence of co-reagents.

Another method is based on the interaction of alkyl ethers of sulfuric or phosphoric acid with cyanates of metals. The reported yield of the isocyanate products is as high as 90% by weight. However, the starting ethers are rarely available and, in some cases, toxic compounds.

Preparation of isocyanates by way of catalytic carbonylation of nitroalkyl compounds requires high temperature within the range of from 100 to 250° C. and pressures of from 100 to 500 atm. The method of preparing isocyanates (with a yield of from 42 to 73%) by decomposition of N-formamides in the presence of chlorine-containing agents has not obtained practical application due to the multi-stage character of the process.

Among phosgene-free methods the Kurcius method is only a laboratory method due to the risk of explosion upon heating of inorganic and organic azides. Also known is preparation of a mono-isocyanate by pyrolysis of esters of carbamic acid in the presence of $P_2O_5$ at a high temperature (100 to 500° C.). However, only low yields were reported by this process.

U.S. Pat. No. 4,192,815 discloses the reaction of primary amines with carbon dioxide and hexamethyldisilazane in the presence of an acidic catalyst to yield silyl esters of carbamic acid, which are then decomposed in the presence of dehydration agents at elevated temperatures. Unfortunately, these esters are decomposed to a mixture of siloxanes, trimethylchlorosilane and mono-isocyanates and must be further purified.

It is apparent from this brief introduction that these alternative methods are limited. They either need to be carried out in dilute solutions using expensive high boiling solvents or require the use of co-reagents and the production of considerable amounts of undesirable by-products. The process used herein is environmentally friendly and does not require any special equipment or novel materials. Furthermore, it leads to aliphatic polyurethanes that are especially suitable for applications that require abrasion resistance and stability against, degradation from UV. These properties are particularly desirable for instance in the exterior paint and enamel coatings industry.

THE INVENTION

Thus, in one embodiment of this invention, there is a process of producing multi-hydroxy polyols. The process comprises providing a comminuted biomass material containing amine groups and hydrolyzing the amine groups to amino acid groups. Thereafter, condensing the amino acid groups with a diamine to produce amine terminated monomers and then reacting the monomers with a carbonate to provide hydroxyl terminated urethane oligomers.

In a second embodiment, there is a process of producing multi-hydroxy polyols as claimed as set forth just Supra, in addition, there is a final step of alkoxylating any carbohydrates in the biomass to produce hydroxyl groups.

In a third embodiment, there is a process of producing multi hydroxy polyols using single amino acids.

In a fourth embodiment, there is a process for producing polymeric materials using the polyol products of this invention. Such polymeric materials include, for example, polyurethanes, polyesters, and polyacetals.

Such polymeric materials can include, for example, rigid foams, flexible foams, semi-rigid foams, flexible molded, foams, binders, fillers, coatings, adhesives, cast elastomers, TPU, auto RIM, sealants, and Spandex, among others.

Proteins and their amino acids that are preferably useful in this invention are proteins from vegetable seeds such as soy, corn (distiller dry grain) jatropha, canola, safflower, and the like. Algae proteins left over after extracting the oil can also be used. In addition, meat proteins, chicken proteins and fish proteins can be used. Especially preferred are seed meals that have had the oil extracted. It is not necessary to separate the proteins or the amino acids to their pure individual components as reproducible and useful polyols are obtained from the mixtures.

Useful carbonates for tis invention are, for example, ethylene carbonate and glycerol carbonate among others.

For the preparation of the polyurethane resins, any isocyanate, catalyst, co-catalyst, surfactant, blowing agent and other fillers known in the art can be used herein. Since the polyols of this invention are self-catalytic, no additional catalyst is really needed.

The inventors herein developed a process for utilizing this relatively inexpensive biomass and convert the amine functional groups to hydroxyl terminated urethanes suitable for use as polyols for rigid polyurethane foams and other uses. The process is relatively simple. It utilizes non-toxic reactants and intermediates and does not require expensive or specialized equipment.

In the process, soy meal is hydrolyzed to a mixture of amino-acids, which are then condensed with ethylene diamine to produce amine terminated monomers. In a second step, these monomers are reacted with ethylene carbonate to yield hydroxyl terminated urethane oligomers. The carbohydrates that are also present in the meal are propoxylated and converted to active polyols. The final polyol mixture is a low viscous liquid having high hydroxyl functionality. These new hydroxyl terminated urethanes can be used to produce rigid foams.

The preparation process and characterization of the soy meal-based polyols is set forth infra, and includes 1H-NMR, FTIR, acid, amine and hydroxyl values) as well as key properties of rigid foams e.g. density, compressive strength, compressive strain at yield, friability, water absorption, burning rate, K factor and dimensional stability with aging.

It was observed that these polyols are much more reactive than conventional polyols, eliminating the need to add a polymerization catalyst in the foaming process. Furthermore, these soy meal-based polyols are compatible with many conventional polyols allowing the formulator to adjust the properties of the foams as needed. Thus, polyurethane foams prepared with 25% and 50% soy meal polyols exhibited comparable properties to foams prepared from a conventional polyol. These new bio-based polyols with self-catalytic properties are suited for rigid spray foam formulations that require fast cure and high crosslink density.

EXAMPLES

Figure 1:
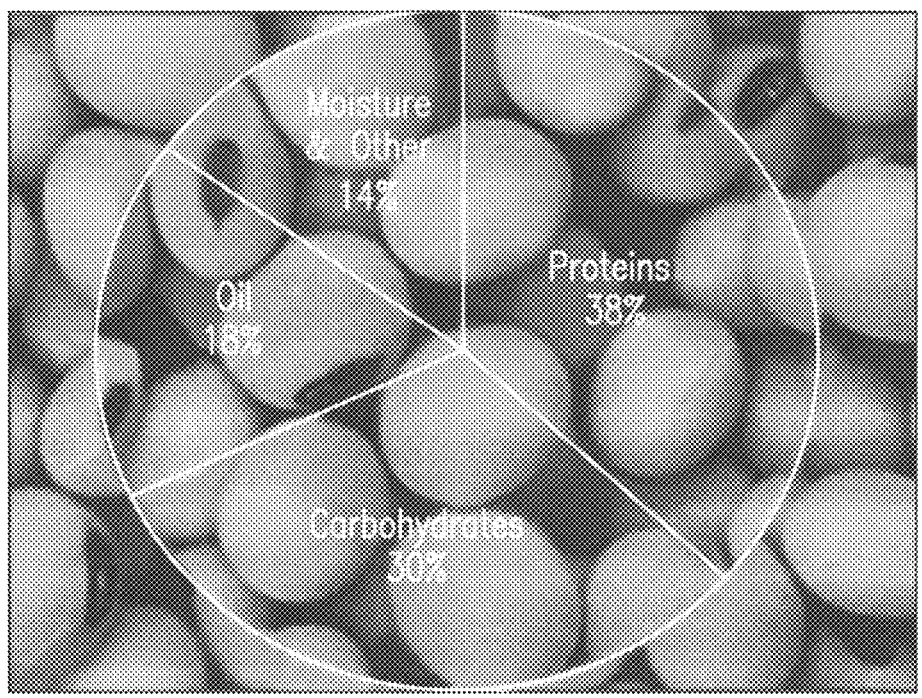
FIG. 1 is chart showing typical soybean composition.

The approach is based on two basic principles: (1). Protect the carboxylic acid by reacting it with ethylene diamine (or similar amines) to form an amide, and (2). React the terminal amines with ethylene carbonate to yield hydroxyl terminated urethanes monomers that can be polycondensed to high molecular weight poly(amide-urethane)s.

The use of ethylene diamine and ethylene carbonate has several advantages: these reactants are inexpensive compounds, their respective reactions are well known and proceed smoothly to high yields and both reactants are readily available and inexpensive materials.

Glycine and L-Arginine amino acids were used as model compounds. Glycine was chosen as it is a simple amino acid containing one amine and one carboxylic acid. L-Arginine was chosen since, it is present in the soy meal at relatively high concentrations and its structure is relatively complex (e.g. it contains two primary amines, one secondary amine and one imine group).

Both of these amino acids exist as zwitterions, which could limit their reactivity. Thus, it was critical to determine if this zwitterionic structure would retard their reactivity. The following is a typical procedure that was used to prepare polyols from L-Argenine (see FIG. 2).

Example 1

L-Arginine (2.3 moles, 400 g), excess ethylenediamine (12.0 moles, 800 ml), and NaOH (8 g, 2 Wt. %) were added to a three-necked round bottom flask fitted with a dean-stark trap topped with a condenser, a thermal sensor for maintaining a constant temperature and a nitrogen inlet. The reaction mixture was refluxed at 113° C. for 60 hours. Unreacted ethylene diamine was removed by distillation to yield L-arginine amido-amine.

In a second step, the intermediate L-arginine amido-amine was reacted with ethylene carbonate (see FIG. 2) to yield hydroxyl-terminated urethane monomer using the following procedure: Arginine amido-amine (290.31 g, 1.34 mole) and ethylene carbonate (293.72 g, 3.34 moles) were added to a 1000 ml three necked flask fitted with mechanical stirrer, thermometer and nitrogen inlet. The reaction mixture was continuously stirred while monitoring the C=O carbonates peak at 1800 cm-1 by FTIR.

A similar procedure was used to prepare a hydroxyl-terminated urethane monomer from Glycine and the amino acids mixture from the hydrolysis of soy meal. Polyols from soy meal required an additional hydrolysis step whereby the proteins in the meal are hydrolyzed to amino acids.

In a typical hydrolysis reaction soy meal (507 g) and 2500 ml 3N HCl were added to a 5000 ml 3-necked round bottom flask fitted with a mechanical stirrer, condenser and nitrogen inlet. The reaction mixture was heated under reflux at 110° C. for 36 hours while stirring. The hydrolyzate was filtered to remove any unreacted humin (105.26 g) and treated with activated carbon to remove some of the dark brown color. The acidic hydrolyzate was neutralized using NaOH to a pH 8 and then vacuum distilled to remove water. The amino acid mixture thus obtained was reacted with ethylene diamine and ethylene carbonate as shown Supra.

Since the soy meal also contains carbohydrates, it was possible to remove them before polymerization. However, it was found that these carbohydrates could be converted to active polyols by reacting them with propylene oxide. This propoxylation reaction is fairly fast and provided a better economics since it eliminated the separation step and allowed higher yield polyols.

In a typical procedure 300 g of the polyol terminated urethane oligomers were placed in a glass reactor and pre-heated to 100° C. The reactor was purged by Nitrogen three times. Each time, nitrogen was removed by vacuum. Finally, 60 g of propylene oxide was added drop wise to the reactor. The vacuum prior to the addition of propylene oxide was kept at −20 psi. Propylene oxide was added such that the temperature was kept below 100° C. and a pressure of +10 psi.

The addition was completed in 5 hours but mixing was continued for an additional 3 hours until the vacuum was close to the initial vacuum indicating complete reaction. It should be emphasized that no catalyst was needed in this process and the presence of the secondary and tertiary amines of the amino acids were sufficient to catalyze this propoxylation reaction.

Example 2

Preparation of Rigid Polyurethane Foams

Water-blown pour-in-place rigid foams were prepared from the soy meal polyols targeting a foam density of 2 pcf. A commercial sucrose-based polyol having hydroxyl value in the range of 360 mg KOH/g was used as a reference polyol. Rigid polyurethane foams were prepared as a control using this polyol in the formulation described in Table 1 and the foams from the soy meal-based polyols were evaluated against this reference foam. All rigid foams were prepared using a standard laboratory procedure using a high-torque mixer. Foams were prepared using water as a sole blowing agent and combination of water with Enovate 3000 (HFC-245fa) blowing agent.

TABLE 1

Typical formulation of rigid foams derived from L-Arginine-polyol

| Sample | Eq. Wt. | control | Foam 1 | Foam 2 | Foam 3 |
|---|---|---|---|---|---|
| Polyol system* | | | | | |
| Jeffol SG-360 | 155.40 | 100 | 50 | 50 | 50 |
| Argenine-based polyol | 114.48 | 0 | 50 | 50 | 50 |
| Water | 9.00 | 4.5 | 4.5 | 4.5 | 4.5 |
| Dabco DC193 | | 2.0 | 2.0 | 2.0 | 2.0 |
| Dabco 33LV | | 1.8 | 0 | 0.8 | 0 |
| Niax A-1 | | 0.1 | 0 | 0 | 0 |
| Dabco T-12 | | 0 | 0 | 0 | 0.05 |
| Isocyanate System | | | | | |
| Rubinate M | 135.50 | 165.55 | 179.41 | 180.49 | 179.41 |
| Isocyanate Index | | 105 | 105 | 105 | 105 |
| Reaction Profile | | | | | |
| Mix time, sec. | | 10 | 10 | 5 | 5 |
| Cream time, sec. | | 13 | 6 | 5 | 6 |
| Gel time, sec. | | 60 | — | — | — |
| Rise time, sec. | | 95 | — | 45 | 55 |
| Tack-free time, sec. | | 105 | 120 | 50 | 50 |

The polyol component of the polyurethane system was prepared by blending the polyol(s) with other formulation components and then the polyol component was mixed with the isocyanate and poured into a paper cup. The foaming profile, including mixing time, cream time, gel time, rise time, and tack-free time were measured for all foams. The foams were aged under room temperature conditions for one week before they were cut and tested. The ASTM test methods that were used to evaluate the properties of the foams are listed in Table 2.

TABLE 2

Foam characterization methods

| Description | Test method |
|---|---|
| Core Density | ASTM D 1622-03 |
| Compressive Strength* | ASTM D 1621-00 |
| Compressive Strain at Yield* | ASTM D 1621-00 |
| Friability by mass loss | ASTM C 421-00 |
| Burning Rate in a Horizontal Position | ASTM D 635-03 |
| Aging Test at 70° C. and Ambient Humidity | ASTM D 2126-99 |
| Aging Test at −30° C. and Ambient Humidity | ASTM D 2126-99 |
| Water Absorption | ASTM D 2842-01 |
| Insulation K-factor* | ASTM C 518-02 |

Table 2: Foam characterization methods
Description of Test methods
Core Density ASTM D 1622-03
Compressive Strength* ASTM D 1621-00
Compressive Strain at Yield* ASTM D 1621-00
Friability by mass loss ASTM C 421-00
Burning Rate in a Horizontal Position ASTM D 635-03
Aging Test at 70° C. and Ambient Humidity ASTM D 2126-99
Aging Test at −30° C. and Ambient Humidity ASTM D 2126-99
Water Absorption ASTM D 2842-01
Insulation K-factor* ASTM C 518-02
RESULTS AND DISCUSSION The soy meal-based polyols as well as the model polyols derived from L-Arginine and Glycine amino acids were viscous liquids at room temperature. These polyols were readily miscible with the other components of the foam formulation as well as many other polyols that are currently being used commercially in the production of rigid foams. Thus, the formulator can easily choose a blend of polyols to achieve specific foam properties.

It should also be emphasized that in all cases a noticeable self-catalytic reaction was noted when the soy meal polyols were used (as well as the polyols derived, directly from the amino acids). The hydrolysis reaction to break the proteins to the individual amino acids is well known and can be accomplished by acid catalysis, ion exchange or by enzymatic reactions.

The rate of the hydrolysis is directly proportional to the temperature and the concentration of acid in the system and only minor effects were observed when different acids were used. The temperature of the reaction can be increased above 100° C. by running the hydrolysis under pressure.

However, it is well known that excessive temperature (as well as excessive concentrations of acid) leads to degradation of the amino acids. We have used relatively mild conditions and, thus, long reaction time to ensure complete hydrolysis and minimum degradation of the resulting amino acids. The composition of the amino acids from the hydrolysis of the soy proteins is well known [8].

Figure 2:
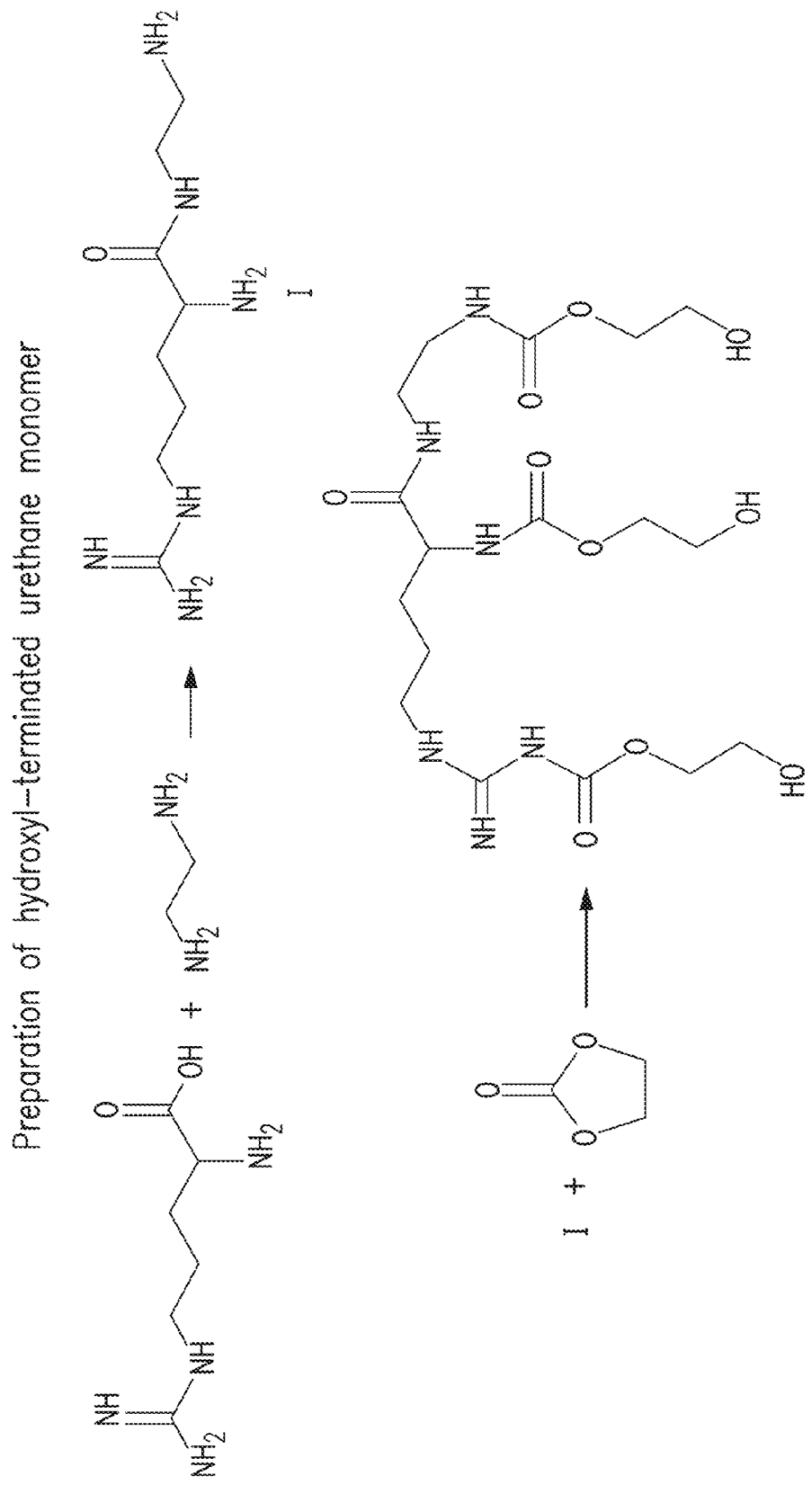
FIG. 2 is a schematic showing the preparation of hydroxyl-terminated urethane monomer.

It was necessary to "protect" the carboxylic acids of the resulting amino acids in order to produce the urethane linkages. This was conveniently done by reacting with ethylene diamine to yield amido-amines derivatives containing terminal amines as shown in FIG. 2. It should be noted however, that excess ethylene diamine for other diamines) is required here, since otherwise both amines of the same molecule will react.

Although this type of dimerization and increase in the molecular weight is not detrimental, it can lead to higher viscosity products. The use of a large excess of ethylene diamine minimized this side reaction. NMR analysis of the product clearly indicated that the amidation reaction proceeded as desired and these data are supported by FTIR spectra that clearly showed a shift of the carbonyl groups from 1640 cm-1 to an amide at 1570 cm-1.

End-group analyses (see Table 3) provided further evidence to the successful sequence of these reactions. The experimental amine and avid values of the model amino acid compound L-Arginine (Arc) are lower than the expected calculated values due to the zwitterion structure, the presence of imine and secondary amine groups.

TABLE 3

End-group analysis

| Sample | Amine value [mg KOH/g] Calc. | Amine value [mg KOH/g] Exp. | Acid value [mg KOH/g] Calc. | Acid value [mg KOH/g] Exp. | OH value [mg KOH/g] Calc. | OH value [mg KOH/g] Exp. |
|---|---|---|---|---|---|---|
| Arg | 644.1 | 336.6 | 322.0 | — | 0.0 | — |
| Arg-ED | 778.1 | 665.1 | 0.0 | 0.0 | 0.0 | — |
| Arg-ED-EC | 0.0 | 103.1 | 0.0 | 0.0 | 480.5 | 448.2 |
| Arg-ED-EC-PO | 0.0 | 74.7 | 0.0 | 0.0 | — | 533.0 |
| SMS | 483.7 | 33.7 | 549.4 | 64.9 | 0.0 | — |
| SMS-ED | 726.7 | 650.4 | 0.0 | 0.0 | 0.0 | — |
| SMS-ED-EC | 0.0 | 58.9 | 0.0 | 0.0 | 456.2 | 454.4 |
| SMS-ED-EC-PO | 0.0 | 49.3 | 0.0 | 0.0 | — | 623.0 |

A significant increase in the amine value was observed after the reaction with ethylene diamine to convert the carboxylic acid groups to amides and produce the diamine derivative (Arg-ED) as shown in FIG. 2. The subsequent reaction with ethylene carbonate led to the formation of the hydroxyl terminated urethane oligomers (Arg-ED-EC) as indicated by the significant drop in the amine value and the high hydroxyl value.

It should be noted here that the amine value did not decrease to zero due to the presence of the less reactive secondary amines and imine groups. However, further reduction in the amine value was obtained by propoxylation (Arg-ED-EC-PO).

Similarly, the hydrolyzed mixture of amino acids from the soy meal (SMS) showed a marked increase in the amine value after similar reaction with ethylene diamine (SMS-ED) followed by high hydroxyl value after the reaction with ethylene carbonate (SMSED-EC). Since the meal also contained carbohydrates, propoxylation led to a significant increase in the hydroxyl value as the propylene oxide reacted with the glucose.

The propoxylation reaction also resulted in a lower viscosity product due to the insertion of short flexible propylene oxide chains that is particularly suitable for rigid polyurethane foams.

The reaction of polymeric methylene diphenyl diisocyanate (Rubinate M, eq. wt.=135.5) with the soy-meal polyols was noticeably faster than the sucrose-based polyols. The presence of secondary amines and, probably imines, catalyzed this reaction. As can be seen from the data in Table 1 where the cream time, gel time, rise time and tack-free time were all significantly shorter than the control polyol.

It was noted that due to this self-catalytic reaction and the high reactivity of these polyols, no amine-based catalysts (Dabco 33LV and Niax A-1) were needed to produce the foams. Typical properties of rigid foams prepared from soy-meal polyol with water as the blowing agent as well as with 1,1,1,3,3-Pentafluoropropane (HFC-245fa) blowing agent are listed in Table 4 and compared with a control foam prepared with Poly-G 74-376, Sucrose/glycerin-based polyol.

It is apparent that the two polyols are completely miscible. The physical properties (e.g. Density, compressive strength, compressive strain and friability) of foams prepared with blends of these polyols are comparable. Similarly, results of the dimensional stability in aging tests at −30° C. and 70° C. up to 2 weeks are essentially identical to the control foams while the flammability measured as burning rate (with no flame retardant additives) is very similar for all these foams, Table 4: Properties of rigid PU foams prepared from propoxylated soy meal urethane polyols Some key advantages of these foams are: low cost raw materials and relatively simple process; readily available and stable source of domestic raw materials; self-catalytic (due to the presence of secondary amines); partially bio-based polyurethane=smaller carbon footprint than traditional rigid foams; high dimensional stability and chemical resistance derived from the amide linkages; compatibility with other polyols, blowing agents and other foam additives, and, low flammability (charring upon burning) in synergy with flame retardant additives.

TABLE 4

Properties of rigid PU foams prepared from propoxylated soy meal urethane polyols

| Sample Designation | Control polyol* | Soy meal polyol | Control polyol* | Soy meal polyol |
|---|---|---|---|---|
| Type of blowing agent | Water | Water | Water- HFC-245fa | Water- HFC-245fa |
| Amount of soy meal polyol [%] | 0 | 25 | 0 | 50 |
| Density, pcf | 2.13 ± 0.19 | 1.62 ± 0.01 | 2.32 ± 0.03 | 2.03 ± 0.07 |
| Compressive Strength, psi | 23.98 ± 2.11 | 17.84 ± 2.06 | 27.65 ± 2.1 | 23.40 ± 2.5 |
| Compressive Strain @ Yield [%] | 6.06 ± 0.38 | 5.44 ± 0.31 | 5.83 ± 0.34 | 4.93 ± 0.71 |
| Friability, mass loss [%] | 5.28 ± 0.03 | 12.99 ± 1.88 | 4.41 ± 0.73 | 8.02 ± 0.26 |

TABLE 4-continued

Properties of rigid PU foams prepared from propoxylated soy meal urethane polyols

| Sample Designation | Control polyol* | | Soy meal polyol | | Control polyol* | | Soy meal polyol | |
|---|---|---|---|---|---|---|---|---|
| | Mass and Volume Change [%] with Aging and Water Immersion Tests | | | | | | | |
| | Mass | Vol. | Mass | Vol. | Mass | Vol. | Mass | Vol. |
| Aging Test @ −30° C. | | | | | | | | |
| after 1 day (24 h) | 0.61 | 0.66 | −0.19 | 0.60 | −0.42 | 0.43 | −0.43 | 0.72 |
| after 1 week (168 h) | 1.69 | 0.88 | 0.93 | 0.17 | 0.98 | 0.11 | −0.14 | 0.49 |
| after 2 weeks (336 h) | 1.53 | −0.55 | 1.12 | 0.24 | 1.41 | 0.10 | −0.14 | −0.30 |
| Aging Test @ 70° C. | | | | | | | | |
| after 1 day (24 h) | −0.31 | 0.78 | 0.19 | −0.29 | −1.23 | 0.09 | −1.04 | −0.33 |
| after 1 week (168 h) | −0.31 | 0.78 | 0.19 | −0.29 | −1.23 | −0.29 | −1.04 | −0.32 |
| after 2 weeks (336 h) | 0.47 | 0.92 | −0.19 | −0.83 | 0.14 | 1.58 | −1.19 | −1.51 |
| Water Absorption @ 25° C. | | | | | | | | |
| after 4 days (96 h) | 217.49 | 0.39 | 304.46 | 2.17 | 165.44 | −0.16 | 252.00 | 6.53 |
| after 1 week (168 h) | 229.73 | 0.73 | 325.84 | 2.14 | 162.04 | 0.14 | 300.15 | 2.44 |
| Burning rate, mm/min | 387 ± 55 | | 380 ± 47 | | 377 ± 35 | | 242 ± 15 | |
| K-factor, BTUs | — | | — | | 0.170 | | — | |
| Density K-factor samples, pcf | — | | — | | 2.62 | | — | |

*Control polyol: Poly-G 74-376, Sucrose/glycerin-based polyol: Hydroxyl value = 361 from Arch Chemicals

What is claimed is:

1. A process of producing polyols, said process comprising:
   a. providing a biomass material comprising proteins;
   b. hydrolyzing said biomass material to amino acids;
   c. condensing said amino acids with a diamine to produce amine terminated monomers;
   d. reacting said monomers with a carbonate to provide hydroxyl terminated urethane oligomers.

2. A process of producing polyols as claimed in claim 1 wherein, in addition, there is a step e. of alkoxylating any carbohydrates in the biomass material comprising proteins to produce hydroxyl groups.

3. A product produced by the process of claim 1.

4. A product produced by the process of claim 2.

5. A process as claimed in claim 1 wherein the biomass material is a meal produced by the extraction of oil from vegetable seed.

6. A process of producing polyols, said process comprising:
   a. providing a material selected from a group consisting essentially of i. proteins, ii. amino acids derived from proteins, and, iii. mixtures of i. and ii.;
   b. condensing any amino acids in said proteins or amino acids derived from said proteins with a diamine to produce amine terminated monomers;
   c. reacting said monomers with a carbonate to provide hydroxyl terminated urethane oligomers.

7. A product produced by the process of claim 6.

8. A process of producing polyols as claimed in claim 6 wherein, in addition, said material contains protein and the process further comprises a step d. of alkoxylating carbohydrates in the protein to produce hydroxyl groups.

9. A product produced by the process of claim 8.

10. A process of producing polyols, the method comprising:
    a. removing any carbohydrates from a biomass material comprising proteins;
    b. hydrolyzing said biomass material to amino acids;
    c. condensing said amino acids with a diamine to produce amine terminated monomers;
    d. reacting said monomers with a carbonate to provide hydroxyl terminated urethane oligomers.

11. A product produced by the process of claim 10.

12. A polyurethane composition produced using the product claimed in claim 3.

13. A polyurethane composition produced using the product claimed in claim 4.

14. A polyurethane composition produced using the product claimed in claim 7.

15. A polyurethane composition produced using the product claimed in claim 9.

16. A polyurethane composition produced using the product claimed in claim 11.

17. A polyester composition produced using the product claimed in claim 3.

18. A polyester composition produced using the product claimed in claim 4.

19. A polyester composition produced using the product claimed in claim 7.

20. A polyester composition produced using the product claimed in claim 9.

21. A polyester composition produced using the product claimed in claim 11.

22. A polyacetal composition produced using the product claimed in claim 3.

23. A polyacetal composition produced using the product claimed in claim 4.

24. A polyacetal composition produced using the product claimed in claim 7.

25. A polyacetal composition produced using the product claimed in claim 9.

26. A polyacetal composition produced using the product claimed in claim 11.

27. The process as claimed in 1 wherein the carbonate is selected from the group consisting essentially of i. ethylene carbonate, ii. propylene carbonate, iii. butylene carbonate, iv. glycerol carbonate, and v. a mixture comprising two or more of i., ii., iii., and iv.

28. The process as claimed in claim 1, wherein the molar ratio of the carbonate to the monomers ranges between 1:10 to 10:1.

29. The process as claimed in claim 28, wherein the molar ratio of the carbonate to the monomers ranges between 1:2 to 2:1.

30. A rigid polyurethane foam which has a foam density in the range from 15 to 65 g/l when produced from the polyol from the process as claimed in claim 1.

31. An insulating rigid foam produced using the product as claimed in claim 3.

* * * * *